United States Patent [19]

Sharp

[11] 4,109,007
[45] Aug. 22, 1978

[54] MITICIDAL MIXTURES AND METHOD UTILIZING A MACROTETROLIDE COMPOUND

[75] Inventor: Silas S Sharp, Wilmington, Del.

[73] Assignee: E. I. Du Pont de Nemours and Company, Wilmington, Del.

[21] Appl. No.: 843,411

[22] Filed: Oct. 20, 1977

Related U.S. Application Data

[60] Continuation-in-part of Ser. No. 818,082, Jul. 22, 1977, abandoned, which is a division of Ser. No. 746,107, Nov. 30, 1976, abandoned.

[51] Int. Cl.² .................. A01N 9/02; A01N 9/20; A01N 9/28
[52] U.S. Cl. .................. 424/279; 424/298; 424/320
[58] Field of Search .................. 424/279, 298, 320

[56] References Cited

U.S. PATENT DOCUMENTS

| 3,530,220 | 9/1970 | Buchanan | 424/320 |
| 3,658,870 | 4/1972 | Buchanan | 260/453 R |
| 3,777,023 | 12/1973 | Sagawa et al. | 424/200 |

Primary Examiner—Allen J. Robinson

[57] ABSTRACT

Miticidal mixtures containing a macrotetrolide compound represented by the formula

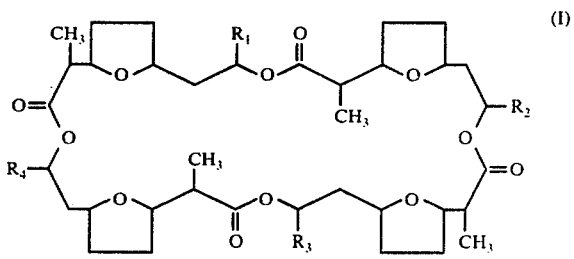

wherein $R_1$, $R_2$, $R_3$ and $R_4$ are each selected from the group consisting of methyl and ethyl, known generically as polynactin and methyl N',N'-dimethyl-N-[(methylcarbamoyl)-oxy]-1-thiooxamimidate (III) known generically as oxamyl, exhibit improved miticidal properties when applied to plants.

3 Claims, No Drawings

MITICIDAL MIXTURES AND METHOD UTILIZING A MACROTETROLIDE COMPOUND

CROSS-REFERENCE TO RELATED APPLICATIONS

This application is a continuation-in-part of my copending application Ser. No. 818,082, filed July 22, 1977 (now abandoned), which in turn is a divisional application of my copending application Ser. No. 746,107, filed Nov. 30, 1976 (now abandoned).

BACKGROUND OF THE INVENTION

This invention relates to miticidal mixtures and method. More particularly, it relates to synergistic miticidal mixtures and method for preventing the destructive effects of pests such as mites in which a macrotetrolide compound represented by the formula

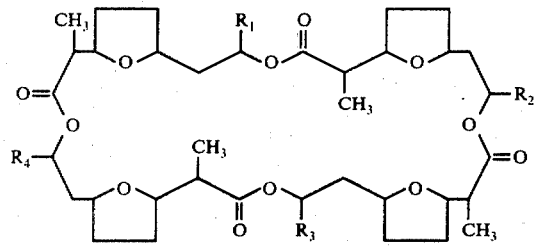

wherein $R_1$, $R_2$, $R_3$ and $R_4$ are each selected from the group consisting of methyl and ethyl and known generically as polynactin is admixed with methyl N',N'-dimethyl-N-[(methyl-carbamoyl)-oxy]-1-thiooxamimidate (III) to achieve improved miticidal properties when applied to plants in significantly smaller amounts than would be required if each of the compounds were applied individually.

The prior art recognizes that certain macrotetrolide compounds may exhibit pesticidal properties individually or when combined with other compounds. U.S. Pat. No. 3,777,023 to Sagawa et al., for example, teaches that miticidal compositions of macrotetrolide antibiotics, such as polynactin, with organochloric, carbamate and organophosphorus pesticides demonstrate increased miticidal activity than the macrotetrolides individually.

U.S. Pat. Nos. 3,530,220 and 3,658,870 to Buchanan disclose that mixtures of certain chemical compounds of the class alkyl 1-carbamoyl-N-(substituted carbamoyl)-thioformimidates such as oxamyl with other acaricides can be useful in preventing plant destruction from insects and mites.

While the above disclosures and others identify effective mite control agents, there is an everpresent need for developing improved miticides and mite ovicides capable of achieving desirable levels of pest control at low cost and high safety margins for the host plant.

SUMMARY OF THE INVENTION

According to this invention it has been discovered that a mixture of

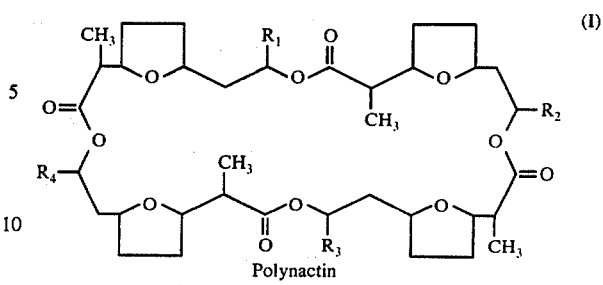

wherein $R_1$, $R_2$, $R_3$ and $R_4$ are each selected from the group of methyl and ethyl with

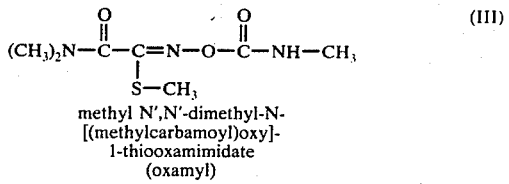

methyl N',N'-dimethyl-N-[(methylcarbamoyl)oxy]-1-thiooxamimidate (oxamyl)

is able to control mites in significantly smaller amounts than would be required if each of the compounds were to be used individually. Thus, a synergistic effect for controlling mites is achieved when compound (I) is admixed with compound (III) and applied to plants using known techniques. By synergistic effect it is meant that the cooperative action of mixtures of compounds I and III is such that the total effect is greater than the sum of the effects of the compounds taken independently.

DETAILED DESCRIPTION OF THE INVENTION

Polynactin consists primarily of the antibiotic tetranactin which is produced by a strain of *Streptomyces aureus*. Four related antibiotics, known generically as nonactin, monactin, dinactin and trinactin are present as minor compounds. The physical and chemical properties and method for preparing polynactin are disclosed in U.S. Pat. No. 3,777,023, the teachings of which are incorporated herein by reference.

In the mixtures of this invention suitable for use as mite control agents, the ratio of compound (III) to compound (I) may range from 50:1 to 2:1, preferably 30:1 to 4:1, and in the most preferred embodiment from 20:1 to 8:1. Ratios are by weight.

The miticidal mixtures of this invention may be applied to plants as sprays or dusts. Ordinarily, however, sprays are used for efficiency and convenience. The sprays may be applied as a light film over plant leaves or to run-off. It is generally desirable to wet plant foliage thoroughly since this assures contact of the miticidally effective compounds with all stages of mites present and greatly enhances the degree of control obtained.

Where mixtures of oxamyl (III) and polynactin (I) are used, high volume applications may contain from about 40 to 1500 ppm of total active ingredient. High volume sprays for field applications to vegetables or fruit trees may contain from about 50 to 1200 ppm of active ingredient; more preferred high volume sprays for this use may contain from about 80 to 1000 ppm of total active ingredient. Most preferred sprays for this use may contain from about 150 to 1000 ppm of the two compounds.

Low volume or ultra low volume sprays may be desired when aerial applications are appropriate. Under such circumstances users can calculate concentrations to be applied based on a knowledge of their equipment and other considerations.

On an area basis in a field situation, from about 0.02–12.5 kg/ha of total active ingredient of these combinations should control most mite problems. It is preferable to use from about 0.05–7 kg/ha. Smaller amounts tend to be useful for mite control in greenhouse applications, due primarily to the significant level of protection provided to the chemicals against the deleterious effects of the weather, e.g., rainfall, sunlight, etc.

These mixtures are especially suited for protection of fruit-bearing trees, nut-bearing trees, ornamentals, vegetable crops, horticultural crops, which would include small fruits and berries and seed crops. Apple trees, peach trees, citrus, cotton, peanuts, beans, strawberries, and ornamentals are particularly susceptible to mite damage in the field; ornamentals, horticultural crops, vegetable crops, are particularly susceptible to mite damage in a greenhouse. Consequently, the mixtures of the instant invention are particularly useful for protection in the previously mentioned areas.

The present invention is further illustrated by the following examples.

EXAMPLE 1

Mite-infested Red Kidney bean plants were sprayed to run-off with polynactin (I) suspensions prepared as described in Example 1, with aqueous dispersions of oxamyl (III), or with oxamyl-polynactin combinations. All sprays contained Surfactant F (Trem 014) at 1:3000 as wetting agent. After spraying, plants were held in the greenhouse. Mite mortality counts were made 48 hours after spraying. The number of live mites per leaf and feeding injury ratings were recorded at the end of 8 days and 2 weeks. The results are recorded below in Table 1.

TABLE 1

| Conc.ppm | | % Kill | Live Mites/Leaf | | Feeding Injury[1] | |
|---|---|---|---|---|---|---|
| III | I | 48 hrs. | 8 days | 14 days | 8 days | 14 days |
| 0 | 0 | 0 | >500 | >500 | 9 | 9.8 |
| 300 | — | 100 | 1 | 6 | 0 | 0 |
| 150 | — | 80 | 58 | 88 | Trace | 0.5 |
| 80 | — | 42 | >500 | >500 | 5 | 7.5 |
| 40 | — | 3 | >500 | >500 | 5 | 9 |
| — | 40 | 77 | 122 | 2 | 1.5 | 1 |
| — | 20 | 34 | >500 | 13 | 2.5 | 3 |
| — | 10 | 3 | >500 | >500 | 4.5 | 7 |
| — | 5 | 0 | >500 | >500 | 4 | 7 |
| 150 | 20 | 100 | 0 | 0 | 0 | 0 |
| 150 | 10 | 99 | 7 | 0 | Trace | 0 |
| 80 | 20 | 100 | 4 | 0 | Trace | 0 |
| 80 | 10 | 100 | 5 | 0 | Trace | Trace |
| 80 | 5 | 93 | 12 | 7 | 0 | 0 |
| 40 | 20 | 99 | 5 | 0 | Trace | 0 |
| 40 | 10 | 100 | 2 | 0 | Trace | Trace |

[1] 0 = no feeding; 10 = leaf destroyed.

EXAMPLE 2

Red kidney bean plants 7–9 days old were infested with two-spotted spider mites by placing on the plants leaf sections cut from infested plants. After 2–4 hours, 50–75 adult mites per leaf transferred to the fresh plants. Each of the infested plants was sprayed to run-off with 50 ml of the desired solution and then held, observing knockdown, 2-, 7-, and 14-day mortality, and plant injury.

The highest rates selected for this test were the lowest found to effective in previous tests (oxamyl, 200 ppm; Polynactin, 10 ppm). When testing combinations of these compounds not more than one-half the minimum effective rate was used. Each test was run in duplicate. The results are recorded below in Table 2 and Table 3.

TABLE 2

| Treatment | ppm *ai | No. Knockdown | % Mortality Days | | | % Injury Compared to Ck. Days | | |
|---|---|---|---|---|---|---|---|---|
| | | | 2 | 7 | 14 | 2 | 7 | 14 |
| Check | — | 1 | 0 | 2 | 11 | — | — | — |
| Oxamyl (III) | 200 | 55 | 100 | 100 | 74 | 10 | 0 | 30 |
| | 100 | 31 | 98 | 20 | 31 | 20 | 50 | 50 |
| | 80 | 11 | 81 | 8 | 36 | 60 | 70 | 70 |
| | 60 | 15 | 37 | 17 | 12 | 60 | 70 | 70 |
| | 40 | 28 | 41 | 26 | 33 | 100 | 100 | 100 |
| Polynactin (I) | 10 | 8 | 16 | 70 | 75 | 60 | 100 | 100 |
| | 8 | 8 | 6 | 30 | 66 | 60 | 100 | 100 |
| | 6 | 0 | 5 | 39 | 50 | 80 | 100 | 100 |
| | 4 | 0 | 1 | 5 | 50 | 80 | 100 | 100 |
| | 2 | 0 | 2 | 5 | 50 | 80 | 100 | 100 |
| Oxamyl + Polynactin | 100 + 1 | 22 | 91 | 21 | 39 | 30 | 60 | 70 |
| | 100 + 2 | 35 | 86 | 31 | 46 | 20 | 30 | 30 |
| | 100 + 3 | 35 | 69 | 69 | 68 | 20 | 20 | 20 |
| | 100 + 4 | 85 | 93 | 88 | 100 | 10 | 10 | 10 |
| | 100 + 5 | 66 | 97 | 100 | 100 | 0 | 10 | 10 |
| | 50 + 5 | 41 | 99 | 97 | 100 | 5 | 10 | 10 |
| | 40 + 5 | 42 | 84 | 90 | 100 | 10 | 10 | 10 |
| | 30 + 5 | 80 | 80 | 90 | 98 | 20 | 20 | 20 |
| | 20 + 5 | 45 | 52 | 40 | 84 | 30 | 40 | 40 |

*ai - active ingredient

TABLE 3

| Treatment | ppm *ai | No. Knockdown | % Mortality Days | | | % Injury Compared to Ck. Days | | |
|---|---|---|---|---|---|---|---|---|
| | | | 2 | 7 | 14 | 2 | 7 | 14 |
| Check | — | 1 | 0 | 2 | 0 | — | — | — |
| Oxamyl (III) | 200 | 22 | 77 | 81 | 48 | 20 | 10 | 10 |
| | 100 | 17 | 50 | 42 | 20 | 30 | 40 | 60 |
| | 80 | 5 | 17 | 7 | 16 | 80 | 100 | 100 |
| | 60 | 7 | 21 | 5 | 7 | 100 | 100 | 90 |
| | 40 | 15 | 20 | 3 | 8 | 100 | 100 | 100 |
| Polynactin (I) | 10 | 5 | 12 | 2 | 63 | 70 | 100 | 100 |

TABLE 3-continued

| Treatment | ppm *ai | No. Knockdown | % Mortality Days | | | % Injury Compared to Ck. Days | | |
|---|---|---|---|---|---|---|---|---|
| | | | 2 | 7 | 14 | 2 | 7 | 14 |
| | 8 | 5 | 5 | 9 | 54 | 80 | 100 | 100 |
| | 6 | 0 | 0 | 3 | — | 70 | 100 | 100 |
| | 4 | 0 | 2 | 2 | 50 | 70 | 100 | 100 |
| | 2 | 0 | 2 | 3 | 59 | 100 | 100 | 100 |
| Oxamyl + | 100 + 1 | 18 | 39 | 18 | 57 | 50 | 60 | 100 |
| Polynactin | 100 + 2 | 41 | 66 | 87 | 55 | 30 | 40 | 50 |
| | 100 + 3 | 56 | 88 | 93 | 91 | 20 | 10 | 10 |
| | 100 + 4 | 72 | 94 | 97 | 91 | 10 | 10 | 10 |
| | 100 + 5 | 103 | 97 | 100 | 100 | 10 | 10 | 10 |
| | 50 + 5 | 76 | 92 | 95 | 100 | 10 | 10 | 5 |
| | 40 + 5 | 78 | 96 | 92 | 100 | 20 | 20 | 5 |
| | 30 + 5 | 43 | 91 | 98 | 99 | 10 | 10 | 10 |
| | 20 + 5 | 83 | 91 | 98 | 100 | 20 | 20 | 5 |

*ai - active ingredient

Useful formulations of compositions containing mixtures of compounds (I) and (III) as active ingredient can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient and at least one of (a) about 0.1% to 20% surfactants and (b) about 1% to 99% solid or liquid diluents. More specifically, they will contain these ingredients in the following approximate proportions:

| | Percent by Weight | | |
|---|---|---|---|
| | Total Active Ingredients | Diluents | Surfactants |
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

J. B. Buchanan, U.S. Pat. No. 3,576,834, Apr. 27, 1971, Col. 5 Line 36 through Col. 7 Line 70 and Ex. 1-4, 17, 106, 123-140.

R. R. Shaffer, U.S. Pat. No. 3,560,616, Feb. 2, 1971, Col. 3 Line 48 through Col. 7 Line 26 and Examples 3-9, 11-18.

E. Somers, "Formulation", Chapter 6 in Torgeson, "Fungicides", Vol. I, Academic Press, New York, 1967.

This invention is further illustrated by the following examples:

EXAMPLE 3

| Dust | |
|---|---|
| oxamyl (III) | 9% |
| polynactin (I) | 1% |
| attapulgite | 10% |
| talc | 80% |

The active ingredient is blended with attapulgite and then passed through a hammer mill to produce particles substantially all below 200 microns. The ground concentrate is then blended with powdered talc until homogeneous.

EXAMPLE 4

| Wettable Powder | |
|---|---|
| oxamyl (III) | 47% |
| polynactin (I) | 3% |
| sodium alkylnaphthalenesulfonate | 2% |
| low viscosity methyl cellulose | 2% |
| diatomaceous earth | 46% |

The ingredients are blended, coarsely hammermilled and then air milled to produce particles of active essentially all below 10 microns in diameter. The product is reblended before packaging.

All mixtures of the invention may be formulated in the same manner.

I claim:

1. A miticidally effective mixture consisting essentially of

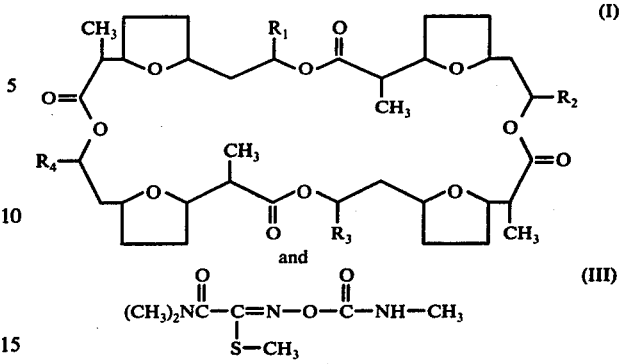

wherein
R₁, R₂, R₃ and R₄ are each selected from the group consisting of methyl and ethyl and
the ratio of III to I is from 4:1 to 16:1.

2. A method for protecting plants from mites comprising applying to the plant locus to be protected a miticidally effective amount of the mixture of claim 1.

3. A composition for the control of mites consisting essentially of a miticidally effective amount of the mixture of claim 1 and at least one of (a) a surface-active agent and (b) a solid or liquid diluent.